(12) United States Patent
Mizutani

(10) Patent No.: US 6,375,644 B2
(45) Date of Patent: Apr. 23, 2002

(54) BODY EXUDATES ABSORBENT ARTICLE HAVING EXPOSED ZONE OF ALTERNATING TROUGHS OR CRESTS

(75) Inventor: Satoshi Mizutani, Kagawa-ken (JP)

(73) Assignee: Uni-Charm Corporation (JP)

( * ) Notice: Subject to any disclaimer, the term of this patent is extended or adjusted under 35 U.S.C. 154(b) by 0 days.

(21) Appl. No.: 09/324,565

(22) Filed: Jun. 2, 1999

(30) Foreign Application Priority Data

Jun. 3, 1998 (JP) ............................................ 10-154588

(51) Int. Cl.⁷ ............................ A61F 13/15; A61F 13/20
(52) U.S. Cl. ........... 604/385.01; 604/380; 604/385.101; 604/385.17; 604/385.21
(58) Field of Search ........................... 604/378, 385.01, 604/379, 385.101, 395, 380, 358, 385.17, 385.21, 385.22, 385.23, 386, 387

(56) References Cited

U.S. PATENT DOCUMENTS

| | | | | | |
|---|---|---|---|---|---|
| 3,343,543 A | * | 9/1967 | Glassman | ................... | 128/290 |
| 4,655,760 A | * | 4/1987 | Morman et al. | ............. | 604/385 |
| 4,775,375 A | * | 10/1988 | Aledo | ........................ | 604/378 |
| 4,891,258 A | * | 1/1990 | Fahrenkrug | ................. | 428/138 |
| 4,895,568 A | * | 1/1990 | Enloe | ....................... | 604/385.2 |
| 5,342,343 A | * | 8/1994 | Kitaoka et al. | ........... | 604/385.2 |
| 5,386,926 A | | 2/1995 | Assier | | |
| 5,389,095 A | * | 2/1995 | Suzuki et al. | ............ | 604/385.2 |
| 5,425,726 A | * | 6/1995 | Shimizu et al. | ........... | 604/385.1 |
| 5,429,632 A | * | 7/1995 | Tanji et al. | ............... | 604/385.2 |
| 5,527,300 A | | 6/1996 | Sauer | | |
| 5,695,487 A | * | 12/1997 | Cohen et al. | ................ | 604/384 |
| 5,779,690 A | * | 7/1998 | Gustafsson et al. | ....... | 604/385.2 |
| 5,795,345 A | * | 8/1998 | Mizutani et al. | ............ | 604/380 |
| 5,810,798 A | * | 9/1998 | Finch et al. | ................ | 604/378 |
| 5,885,264 A | * | 3/1999 | Matsushita | ................... | 604/361 |
| 5,895,380 A | * | 4/1999 | Turi et al. | ................... | 604/383 |
| 5,928,212 A | * | 7/1999 | Kline et al. | ................. | 604/391 |
| 6,077,254 A | * | 1/2000 | Silwanowicz et al. | ... | 604/385.2 |

FOREIGN PATENT DOCUMENTS

DE 4422956 A1 9/1996

* cited by examiner

Primary Examiner—John G. Weiss
Assistant Examiner—Michele Kidwell
(74) Attorney, Agent, or Firm—Baker & Daniels

(57) ABSTRACT

A body exudates absorbent article including a liquid-absorbent core having transversely opposite side edges extending in parallel to each other in a longitudinal direction of the article, a liquid-pervious topsheet covering an upper surface of the core and a liquid-impervious backsheet covering a lower surface of the core, the topsheet being formed in a zone covering the core with a plurality of alternating troughs and crests continuously undulating in a transverse direction of the article and these troughs and the crests extending in the longitudinal direction, and thereby maintaining an initial soft elasity of the topsheet.

8 Claims, 3 Drawing Sheets

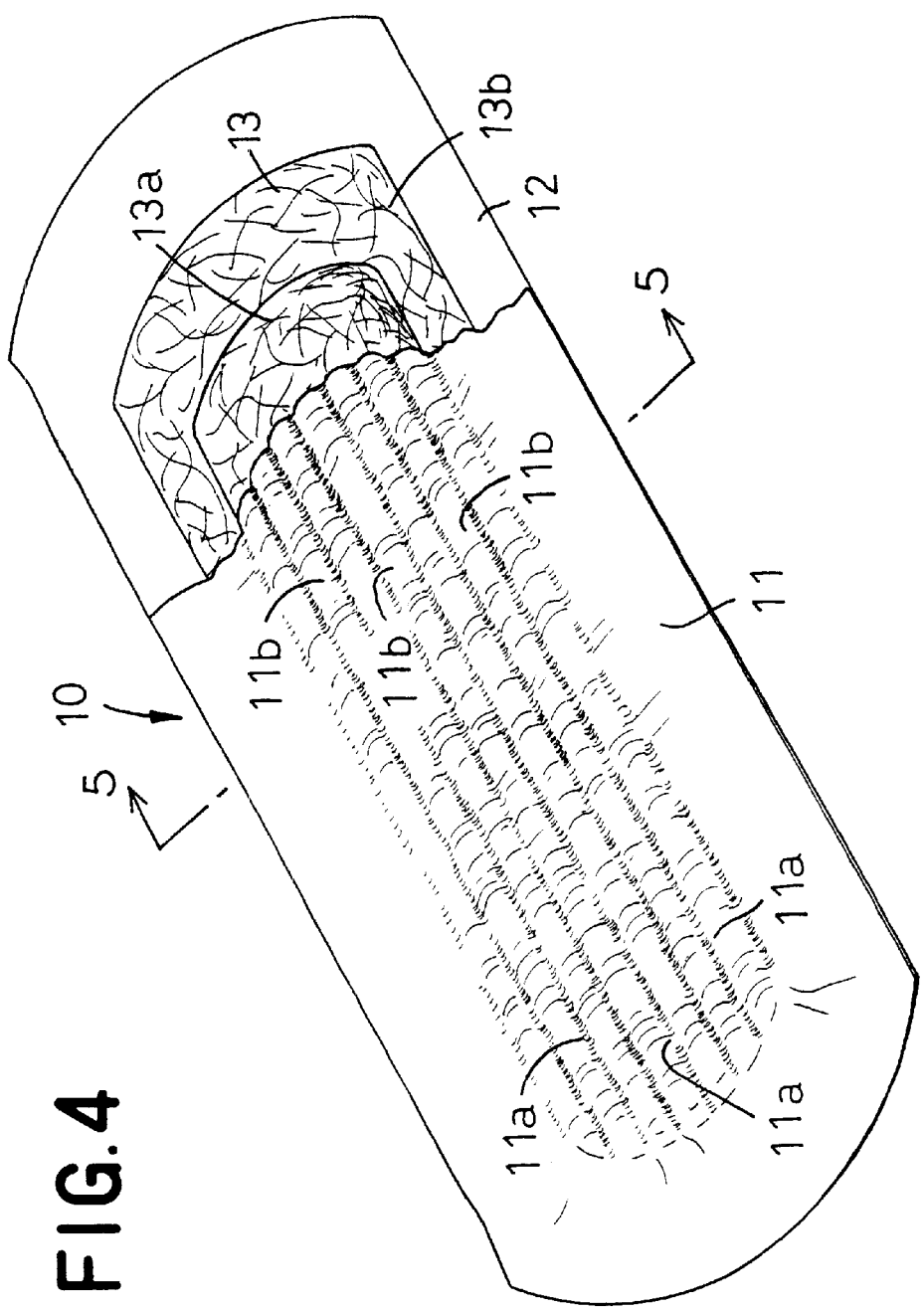

BODY EXUDATES ABSORBENT ARTICLE HAVING EXPOSED ZONE OF ALTERNATING TROUGHS OR CRESTS

BACKGROUND OF THE INVENTION

This invention relates to a body exudates absorbent article such as a sanitary napkin, a blood absorbent pad, an incontinent pad, a disposable diaper and the like.

Body exudates absorbent articles such as sanitary napkins or disposable diapers generally comprises a liquid-pervious topsheet, a liquid-impervious backsheet and a liquid-absorbent core disposed between these two sheets. The topsheet is usually made of a nonwoven fabric or a synthetic resin film.

Touch of such article during its actual use can be improved by using a soft and elastic nonwoven fabric. However, if so-called convex core which is convex only in its transversely middle zone is adopted in such article, a nonwoven fabric is forcibly pressed against said convex middle zone of the core and, in consequence, an initial soft elasticity of nonwoven fabric may be lost. On the other hand, a synthetic resin film can not be expected to offer the soft elasticity of a nonwoven fabric.

SUMMARY OF THE INVENTION

In view of the problem as has been described above, it is an object of the present invention to provide a body exudates absorbent article adapted to maintain a soft elasticity of a topsheet in spite of a liquid-absorbent core of a so-called convex type adopted in the article.

According to the present invention, there is provided a body exudates absorbent article comprising a liquid-absorbent core having transversely opposite side edges extending in parallel to each other in a longitudinal direction of the article, a liquid-pervious topsheet covering an upper surface of the core and a liquid-impervious backsheet covering a lower surface of the core, wherein the topsheet is formed in a zone covering the core with a plurality of alternating troughs and crests continuously undulating in a transversely direction of the core and the troughs and crests extend in the longitudinal direction.

With the body exudates absorbent article according to the present invention, the amount of body exudates discharged on the napkin flows into and spreads along the respective troughs and is prevented by the crests functioning as barriers from leaking sideways. Both the troughs and the crests easily restore their initial configurations as well as their initial soft touch immediately after their deformation due to a shift of the topsheet or some external pressure exerted thereon.

In spite of the convex configuration of the core adopted by the article, the unique arrangement according to the present invention facilitates the topsheet to be transversely stretched without compressing the convex top of the core and thereby enables a soft elasticity of the core to be maintained.

Consequently, the body exudates absorbent article according to the present invention allows a skin-contactable surface (i.e., the body surface) of the article to be reliably placed in close contact with the wearer's labium and thereby ensures the body exudates discharged thereon to be prevented from leaking through a gap which might otherwise formed between the absorbent surface and the wearer's labium.

BRIEF DESCRIPTION OF THE DRAWINGS

FIG. 4 is a view similar to FIG. 1 showing another embodiment of the sanitary napkin according to the present invention.

DETAILED DESCRIPTION OF THE PREFERRED EMBODIMENTS

Details of a body exudates absorbent article according to the present invention will be more fully understood from the description of a sanitary napkin as a specific embodiment given hereunder with reference to the accompanying drawings.

Figure 1:
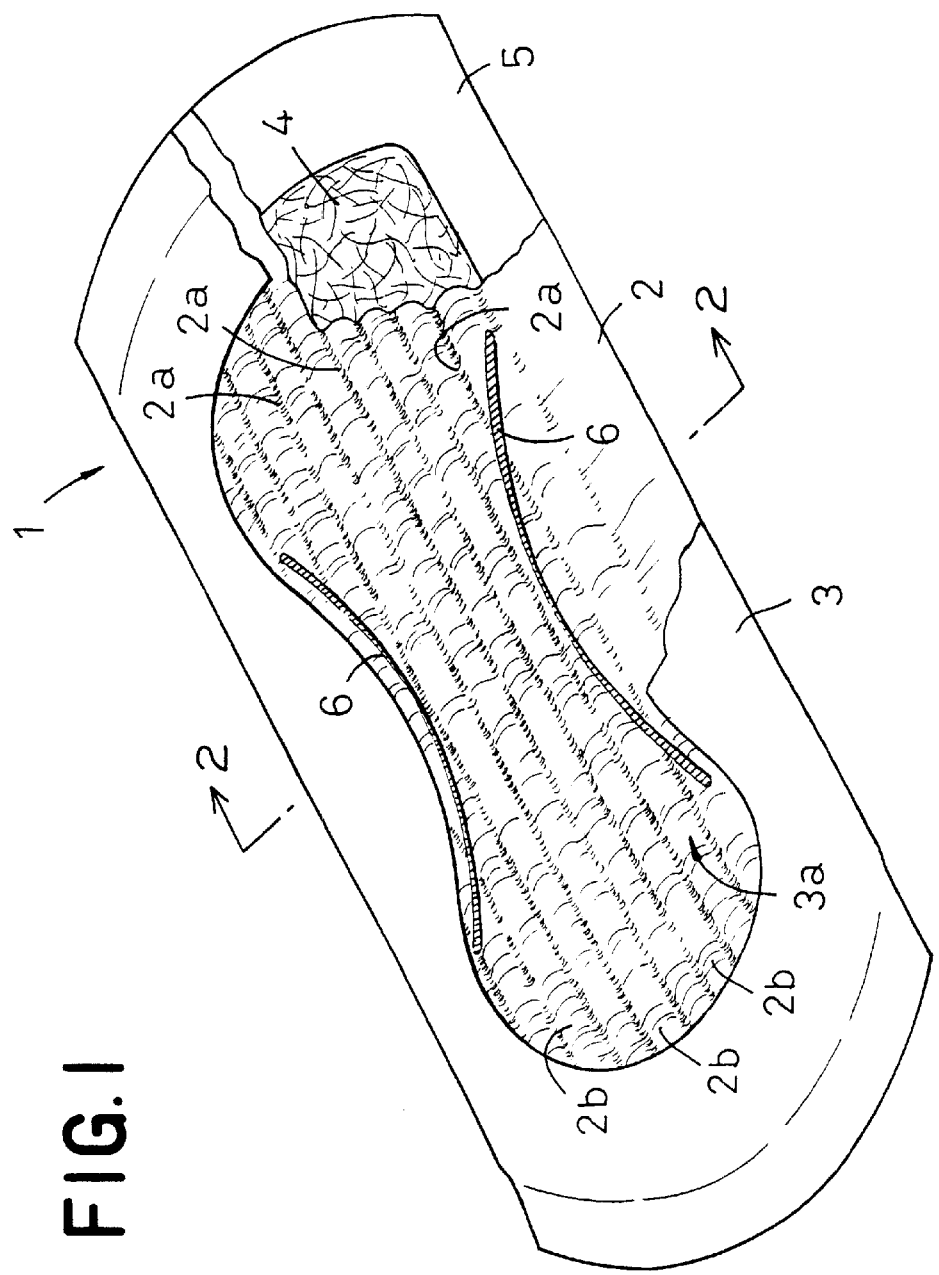
FIG. 1 is a perspective view showing an embodiment of a sanitary napkin according to the present invention as partially broken away.
Figure 2:
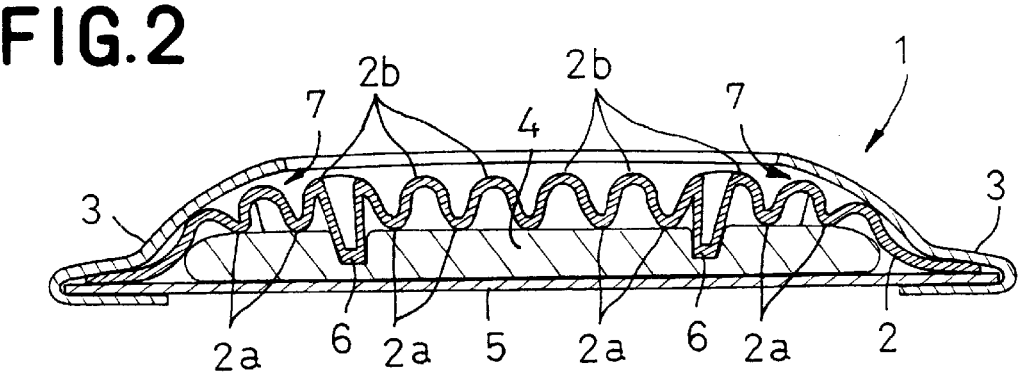
FIG. 2 is a sectional view taken along a line A—A in FIG. 1.

FIG. 1 is a perspective view showing a sanitary napkin as partially broken away and FIG. 2 is a sectional view taken along a line A—A in FIG. 1. A sanitary napkin 1 comprises a liquid-pervious topsheet 2, a liquid-impervious backsheet 5, a liquid-absorbent core 4 disposed between these two sheets 2, 5, and a barrier cover sheet 3.

A region of the topsheet 2 covering the core 4 is formed with a continuous undulation extending transversely of the core 4, which undulation comprises alternating troughs 2a and crests 2b each extending longitudinally of the core 4. While it is not essential to bond bottoms of the troughs 2a to an upper surface of the core 4, the bottoms of the troughs 2a are preferably bonded to the upper surface of the core 4 in order that the undulation can be easily restored even after the troughs 2a and crests 2b are buckled under external pressure. Obviously, it is also possible to form the topsheet 2 with the troughs 2a and crests 2b in the entire region of the topsheet 2 covering the core 4. However, a desired effect of the troughs 2a and crests 2b can be obtained even when they are formed only in a region of the topsheet 2 covering a central zone of the core 4 and not its peripheral zone.

The topsheet 2 and the backsheet 5 have their inner surfaces bonded to each other by means of adhesive agent or heat-sealing technique along their portions extending outward beyond longitudinally opposite ends as well as along their portions extending outward beyond transversely opposite side edges of the core 4. The topsheet 2 and the core 4 are bonded together by a pair of compressed grooves 6, 6 respectively extending along the side edges of the core 4.

The compressed grooves 6, 6 really lie slightly inside the side edges of the core 4 and are convexly curved toward a middle of the core 4. The compressed grooves 6, 6 function to prevent the topsheet 2 and the core 4 from being spaced from each other during actual use of the napkin 1.

The barrier cover sheet 3 covering an upper surface of the napkin 1 along its outer peripheral zone has transversely opposite side edges folded back onto the backsheet 5 and is bonded to an outer surface of the backsheet 5 by means of adhesive agent or heat-sealing. The barrier cover sheet 3 is formed in its zone corresponding to the central zone of the core 4 with a longitudinally larger opening 3a through which the troughs 2a and the crests 2b of the topsheet 2 are exposed. Along a periphery of the opening 3a, the topsheet 2 and the barrier cover sheet 3 are not bonded to each other so that a pocket 7 serving to receive body exudates and prevent from leaking may be formed between these two sheets 2, 3. Though not shown, at least transversely opposite side edges of the opening 3a making a part of the periphery may be provided with stretchable/contractable elastic members functioning to lift the opening 3a off from the topsheet 2.

Figure 3:
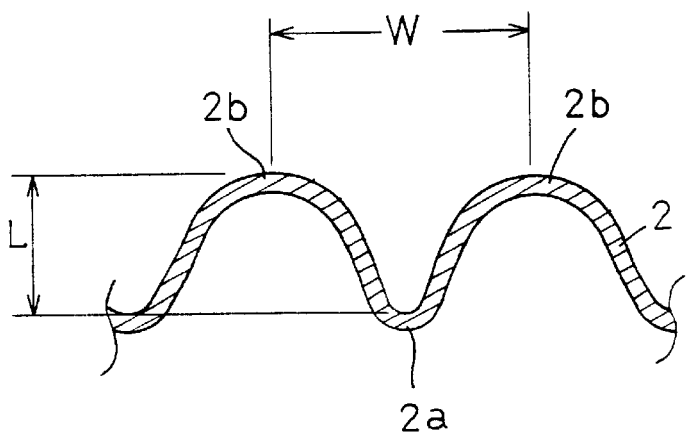
FIG. 3 is a fragmentary sectional view of a topsheet, showing a trough and a crest.

FIG. 3 is a fragmentary sectional view of the topsheet 2, showing the trough 2a and the crest 2b. Referring to FIG. 3, a height L as measured from a bottom of the trough 2a to an apex of the crest 2b is 1.5~10.0 mm, preferably 3.0 10.0 mm. The height L being less than 1.5 mm would facilitate an amount of body exudates to flow beyond the crests 2b transversely of the napkin and cause the amount of body exudates to leak sideways. A distance W between each pair of the adjacent crests 2b is 1.0~15.0 mm, preferably 5.0~15.0 mm. It is also possible to form the troughs 2a and the crests 2b so that the height L as well as the distance W may be varied depending on the zones of the topsheet 2 covering the core 4. Specifically, the troughs 2a and crests 2b are formed in the central zone of the topsheet 2 so that their height L as well as their distance W are larger than those of the troughs 2a and the crests 2b formed in a peripheral zone of the topsheet 2.

The topsheet 2 may be made of a hydrophilic nonwoven fabric, for example, a hydrophobic nonwoven fabric treated with suitable agent making the nonwoven fabric hydrophilic or nonwoven fabric comprising fibers into which such agent has been kneaded. The nonwoven fabric used as the material for the topsheet 2 preferably comprises conjugated fibers which has been crimped by a heat treatment and thereby has a high cushioning effect.

Fineness of such fibers is preferably in a range of 1~6 deniers. Basis weight of the nonwoven fabric is preferably in a range of 20~80 g/m$^2$, more preferably in a range of 30~80 g/m$^2$. The topsheet 2 may also comprise a laminate of an upper layer nonwoven fabric having a relatively low density per unit area and a lower layer nonwoven fabric having a relatively high density per unit area. For example, the upper layer may be a nonwoven fabric having a fineness of 4 deniers and a basis weight of 20 g/m$^2$ and the lower layer may be a nonwoven fabric having a fineness of 2 deniers and a basis weight of 40 g/m$^2$. With the topsheet 2 of such an arrangement, a permeation rate for body exudates in an upper layer nonwoven fabric is higher than that in a lower layer nonwoven fabric. By permeating body exudates from an upper layer nonwoven fabric to the lower layer nonwoven fabric as rapidly as possible, an amount of body exudates which might stay on the outer surface of the topsheet 2 can be eliminated or minimized.

The core 4 comprises a mixture of fluff pulp and superabsorptive hydrogel particles, the mixture being completely covered with a tissue paper and compressed to a desired thickness.

Figure 5:
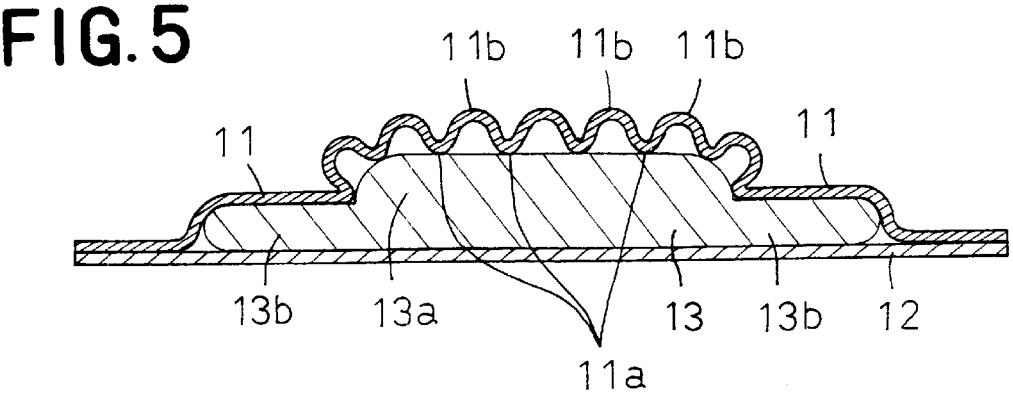
FIG. 5 is a sectional view taken along a line B—B in FIG. 4.

FIG. 4 is a view similar to FIG. 1, showing a sanitary napkin 10 embodied in an alternative manner and FIG. 5 is a sectional view taken along a line B—B in FIG. 4. The sanitary napkin 10 comprises a liquid-pervious topsheet 11, a liquid-impervious backsheet 12 and a liquid-absorbent core 13 disposed between these two sheets 11, 12 and bonded to an inner surface of at least one of these two sheets 11, 12.

The core 13 disposed between the topsheet 11 and the backsheet 12 has a convex configuration defined by a 3b transversely middle zone 13a and a peripheral zone 13b which is lower than the transversely middle zone 13a. The topsheet 11 is formed in its zone lying above the middle zone 13a of the core 13 with alternating troughs 11a and crests 11b each extending longitudinally of the core 13 and continuously undulating transversely of the core 13. The topsheet 11 is bonded to an upper surface of the core 13 along its peripheral zone 13b but not in the middle zone 13a, by means of adhesive agent (not shown). The topsheet 11 has its portions extending outward beyond longitudinally opposite ends and extending outward beyond transversely opposite side edges of the core 13, respectively, bonded to the backsheet 12 by means of adhesive agent or heat-sealing technique.

In the middle zone 13a of the core 13, the bottoms of the respective troughs 11a are not bonded to the upper surface of the core and therefore the topsheet 11 can be transversely stretched by a desired dimension in the middle zone 13a of the core when the topsheet 11 and the backsheet 12 are bonded together along a peripheral edge of the napkin 10. With an advantageous consequence, in spite of the arrangement that the convex core 13 is sandwiched between the topsheet 11 and the backsheet 12, the top of the core 13 is never compressed and an initial softness of the core 13 can be maintained. On the contrary, the troughs 11a and the crests 11b of the topsheet 11 function as a cushion in the middle zone 13a of the core 13 and give the wearer a soft touch.

A height as measured from the bottom of the trough 11a to the apex of the crest 11b of the topsheet 11 is preferably in a range of 1.5~4.0 mm. A distance between each pair of the adjacent crests 11b is preferably in a range of 2.0~10.0 mm.

What is claimed is:

1. A body exudates absorbent article comprising:
   a liquid-absorbent core having transversely opposite side edges extending in parallel to each other in a longitudinal direction;
   a liquid-pervious topsheet covering an upper surface of said liquid-absorbent core; and
   a liquid-impervious backsheet covering a lower surface of said liquid-absorbent core,
   said liquid-pervious topsheet and said liquid-impervious backsheet having inner surfaces that are bonded to one another along portions thereof that extend outward beyond longitudinally opposite ends of said liquid-absorbent core and outward beyond opposite side edges of said liquid-absorbent core,
   said liquid-pervious topsheet being formed in a zone covering said liquid-absorbent core with a plurality of alternating troughs and hollow crests continuously undulating in a transverse direction of said article and said troughs and hollow crests extending in said longitudinal direction,
   said liquid-absorbent core and said liquid-pervious topsheet being bonded to each other along a pair of compressed grooves which extend in said longitudinal direction in proximity to said transversely opposite side edges of said liquid-absorbent core,
   an upper surface of said liquid-pervious topsheet being covered with a barrier cover sheet which is formed in a zone corresponding to a central zone of said liquid-absorbent core with a longitudinal larger opening through which said troughs and said hollow crests of said liquid-pervious topsheet are exposed, said pair of compressed grooves lying in proximity to lateral side edges of said opening.

2. A body exudates absorbent article according to claim 1, wherein a height as measured from a bottom of each said troughs to an apex of each said hollow crests is in a range of about 1.5 to about 10.0 mm and a distance between pairs of adjacent ones of said hollow crests is in a range of about 1.0 to 15.0 mm.

3. A body exudates absorbent article according to claim 1, wherein a transversely middle zone of said liquid-absorbent core is configured to be higher than a peripheral zone of said liquid-absorbent core.

4. A body exudates absorbent article according to claim 1, wherein transversely opposite side edges of said barrier cover sheet are folded back onto said liquid-impervious backsheet and bonded to an outer surface of said liquid-impervious backsheet.

5. A body exudates absorbent article according to claim 1, wherein a pocket is formed between said liquid-pervious topsheet and said barrier cover sheet along a periphery of said opening.

6. A body exudates absorbent article according to claim 1, wherein said pair of compressed grooves lie inside the lateral side edges of said opening.

7. A body exudates absorbent article according to claim 1, wherein said pair of compressed grooves and the lateral side edges of said opening are convexly curved toward a middle of said liquid-absorbent core.

8. A body exudates absorbent article according to claim 3, wherein said troughs and said hollow crests are formed only in said transversely middle zone of said liquid-absorbent core which is configured to be higher than the peripheral zone of said liquid-absorbent core.

* * * * *